United States Patent
Zakoshansky et al.

(10) Patent No.: US 7,393,984 B1
(45) Date of Patent: Jul. 1, 2008

(54) METHOD FOR PRODUCTION OF CUMENE HYDROPEROXIDE

(75) Inventors: Vladimir Zakoshansky, Long Grove, IL (US); Irina Vassilieva, St. Petersburg (RU); Andrey Budarev, St. Petersburg (RU); Vasiliy Trubaev, St. Petersburg (RU); Sergey Korchagin, Novokuznetsk (RU)

(73) Assignee: ILLA International, LLC, Reno, NV (US)

(*) Notice: Subject to any disclaimer, the term of this patent is extended or adjusted under 35 U.S.C. 154(b) by 0 days.

(21) Appl. No.: 11/934,032

(22) Filed: Nov. 1, 2007

(51) Int. Cl.
  *C07C 409/14* (2006.01)
(52) U.S. Cl. .................................. 568/569
(58) Field of Classification Search .............. None
  See application file for complete search history.

(56) References Cited

U.S. PATENT DOCUMENTS

| | | | |
|---|---|---|---|
| 5,767,322 A | 6/1998 | Zakoshansky et al. | |
| 5,908,962 A | 6/1999 | Zakoshansky et al. | |
| 6,956,136 B2 | 10/2005 | Dyckman et al. | |

FOREIGN PATENT DOCUMENTS

SU  1455596  7/1987

OTHER PUBLICATIONS

B.D. Kruzhalov, Combined Fabrication of Phenol and Acetone, Book, 1963, 110 and 111, Government Scientific & Technical Publisher of Chemical Literature, Moscow.

*Primary Examiner*—Rosalynd Keys
(74) *Attorney, Agent, or Firm*—Edward Etkin, Esq.

(57) ABSTRACT

A continuous method of cumene oxidation in a gas-liquid system is provided, where the liquid phase is represented by cumene and its oxidation products and the gas phase is represented by air. The oxidation process can be carried out either in a reactor series or in a single reactor at least one of which is preferably equipped with at least two airlift-type trays. When specific CHP concentration is achieved, the oxidation products are discharged from the to reaction zone and treated in a mixing device with aqueous ammonia or water to remove organic acids such as formic acid, benzoic acid, etc. and to remove phenol, which is an inhibitor of oxidation reaction. The cumene oxidation product stream, free of organic acids and phenol is recycled to the same reactor in the case of single reactor, or is passed to the next reactor of the series in the case of reactor series. In all cases, the oxidation products treated with water or aqueous ammonia is first directed to a unit for separation of aqueous phase from organic products and then anhydrous organic product stream is forwarded to the next reactor of the series, or recycled to the single reactor for the continued cumene oxidation until the required CHP concentration is achieved. The airlift-type trays in at least one process reactor accelerate the cumene oxidation reaction therein while increasing the process selectivity and enabling the process to be conducted at lower temperature, improving safety thereof. Advantageously, lower quality cumene having impurities such as sulfur-containing trace elements, can be used in the inventive process while maintaining a high process selectivity.

20 Claims, 2 Drawing Sheets

METHOD FOR PRODUCTION OF CUMENE HYDROPEROXIDE

CROSS REFERENCE TO RELATED APPLICATION

This application is related to a co-pending commonly assigned provisional patent application entitled "Method for Acceleration of Cumene Oxidation", filed Nov. 1, 2007, which is hereby incorporated by reference herein in its entirety.

FIELD OF THE INVENTION

This invention relates to the field of the commercial manufacture of petrochemical synthesis products, and in particular, to a method of production of cumene hydroperoxide to further decompose it into phenol and acetone.

BACKGROUND OF THE INVENTION

Cumene hydroperoxide (hereinafter "CHP") is commonly produced using one or more well known methods of oxidation of cumene with air oxygen at a high temperature, i.e., oxidation takes place in liquid-gas system. Typically, cumene is oxidized until CHP concentration reaches 20-35 wt. %, because further increase in cumene conversion leads to a significant build-up of by-products resulting in a proportionally lower process selectivity. The oxidation products are then delivered to a vacuum stripping stage where unreacted cumene is distilled. The stripping bottom product containing about 60-93 weight percent of CHP is then delivered to a CHP cleavage stage, where CHP decomposes into acetone and phenol under influence of an acidic catalyst. It is well known that in conventional oxidation processes, the main CHP formation reaction is accompanied by a number of side reactions.

The effect of side reactions on the main CHP formation reaction depends, among other factors, on process conditions such as one or more of the following: temperature, product residence time in the reactors, and cumene conversion degree. Typically, the main by-products formed in the side reactions are dimethylbenzene alcohol (hereinafter 'DMBA'), acetophenone (hereinafter "AP") to and organic acids, such as formic acid, acetic acid, and/or benzoic acid. Formic and benzoic acids serve to catalyze the acidic decomposition of CHP to form phenol and acetone.

The presence of phenol in the reaction products, under the conditions of a radical oxidation process, is extremely undesirable because it results in a dramatic inhibition of the CHP formation reaction and has a significant negative impact on the overall process selectivity. In fact, research has demonstrated that when employing conventional previously known process technologies, (i.e. without special treatment of the cumene oxidation products with ammonia), the rate of oxidation of low-quality cumene (in which sulfur-containing trace contaminants are present) is so slow that such conventional technologies could scarcely be considered acceptable for commercial processes. Moreover, when the CHP concentration reaches about 20 wt. %, the conversion of cumene starts to decrease, which leads to complete termination of the reaction. The undesirably low rate of reaction at the initial period is a result of the presence of inhibitors that are contained in the cumene, (most commonly, sulfur-containing contaminants). Specifically, the reason for the inevitable slow-down of the oxidation rate over a course of time, is the joint influence on the reaction of inhibitors accumulated in the reactor due to the oxidation reaction itself, as well as inhibitors introduced with fresh cumene. In fact, the rate of formation of radicals in the reactor turns out to be slower than the rate of the radical chain propagation, which leads to the suppression of the process.

There are several ways to avoid the formation of phenol as oxidation inhibitor. Most of them are well known in the art and involve the use of alkali agents such as hydroxides of alkaline metals and their carbonates as well as high molecular carbon salts at cumene oxidation. Such methods are described in greater detail in the U.S. Pat. No. 3,187,055 issued Jun. 1, 1965, and in the U.S. Pat. No. 2,796,439 issued Jun. 18, 1957.

A general disadvantage of previously known methods (for example, such as described in the above-identified patents) is the need for careful separation of added reagents from the oxidation products formed during the reaction, which is a difficult practical engineering problem. This separation is essential because the presence of added reagents has an adverse impact on further stage of CHP concentration by increasing the expressiveness of the process and initiating partial decomposition of CHP into byproducts such as DMBA and Acetophenone. The overall CHP losses to the byproducts can be about 1-1.5% (absolute), which is impermissible and undesirable in most large-scale process. Furthermore, the presence of alkali compounds, not only dramatically complicates the stage of acidic CHP decomposition into phenol and acetone, but also exposes this stage to significant potential dangers.

Other methods of cumene oxidation—for example in the presence of aqueous solutions of alkaline agents—are also known in the art and are disclosed in U.S. Pat. No. 2,663,740, issued Mar. 5, 1952, USSR Author's certificate No. 567723, filed May 16, 1975, and in USSR Author's certificate No. 858313, filed Aug. 21, 1981. The above-mentioned alkaline agents and carbonates of alkaline agents as well as ammonia and tetralkylammonia base solutions are related to the aqueous solutions of alkaline agents. Thus, these to methods of the oxidation process conduction are not free of the above-described disadvantages.

There are also known methods of continuous cumene oxidation to CHP in without use of catalysts, initiators, and alkaline agent additives where the mixture of initial and recycle cumene streams is treated from impurities inhibiting the oxidation process by washing the mixture with aqueous sodium hydroxide and water solution. One such method is disclosed in U.S. Pat. No. 3,907,901; issued on Sep. 23, 1975. However, the disadvantages of this, and similar methods are:

1) A low feed oxidation rate (e.g., 1.5-2 weight % t per hour) that requires an increase in the reaction volume of the reactors to provide the required unit productivity (this also results in higher process costs); and 2) Low process selectivity with regard to desired product (91-92 mole %).

The Russian patent No. 2146670, published on Mar. 20, 2000, proposes a solution by which the problem of selectivity, and therefore minimization of losses at CHP concentration stage, is resolved by the division of the process into two steps. At the first step, the process is carried out with pure cumene, freed from alkaline agents. A base, such as $NH_4OH$, is added into a first reactor of a series of sequential reactors and supplied with water. Cumene oxidation products coming out from a last series reactor are forwarded to a CHP concentration stage, and recycle cumene streams from the CHP concentration stage, an off-gas condensation stage, and an alphamethylstyrene (hereinafter "AMS") hydrogenation stage, are treated with NaOH, ($NH_4NaCO_3+NH_4OH$), $NH_4OH$ and $H_2O$ in a technologically complicated scheme.

Although a sufficiently high selectivity was achieved by implementing this process without discharging of the process inhibitor (specifically, phenol), and injection of water into the reactor, the rate of CHP formation in the reactors is relatively low, i.e. 2.8 wt. % to 3.0 wt. % per hour. This approach requires the use of very large reactor volumes, and therefore results in significantly higher capital investment in implementing the process. In cases of revamps of existing plants, high volume reactors may make this process impossible to implement due to space considerations.

Other inhibitors of CHP formation reaction (such as sulfur-containing trace contaminants, etc.) that may be present as a result of utilization of lower-grade cumene, also have a considerable negative effect on the process. In fact, research has demonstrated that when employing most conventional previously known process technologies, (i.e., without special treatment of the cumene oxidation products with ammonia), the rate of oxidation of low-quality cumene (in which sulfur-containing trace contaminants are present) is so slow that such conventional technologies could scarcely be considered acceptable for commercial processes.

Moreover, when the CHP concentration reaches about 20 wt. %, the conversion of cumene starts to decrease, which leads to complete termination of the reaction. The undesirably low rate of reaction at the initial period is a result of the presence of inhibitors that are contained in the cumene, (most commonly, sulfur-containing contaminants). Specifically, the reason for the inevitable slow-down of the oxidation rate over a course of time, is the joint influence on the reaction of inhibitors accumulated in the reactor due to the oxidation reaction itself, as well as inhibitors introduced with fresh cumene. In fact, the rate of formation of radicals in the reactor turns out to be slower than the rate of the radical chain propagation, which leads to the undesirable suppression of the process.

It would thus be desirable to provide a process for production of CHP that is capable of producing CHP at a higher process selectivity, with greater safety, and lower expense than previously known techniques. It would also be desirable to provide a process for production of CHP that is capable of utilizing lower-grade cumene comprising oxidation process inhibiting trace elements (e.g., sulfur-containing trace compounds, etc.), while producing CHP at a substantially the same or higher process selectivity than any of the previously known processes utilizing a higher grade of cumene in CHP production. It would moreover be desirable to provide a process for producing CHP, that decreases the amount of preexisting and by-product process inhibitors during the cumene oxidation reaction, thereby raising the process selectivity and improving process safety.

SUMMARY OF THE INVENTION

The object of the present invention is to eliminate the above-described disadvantages of previously known CHP production methods, and to provide a safe method for producing CHP with a high productivity, a high degree of selectivity; and at a lower expense. In brief, in accordance with the inventive process, cumene oxidation is conducted in liquid-gas system, where cumene and cumene oxidation products act as a liquid phase and air acts as a gas phase. The inventive process utilizes one or more sequential reactors to conduct cumene oxidation while removing and reducing the formation of undesirable reaction-inhibiting by-products. In each reactor (or during each repeated reaction cycle if a single reactor is utilized), CHP concentration is monitored during the oxidation reaction, and, when a predetermined threshold CHP concentration is reached, at least a portion of the oxidation products are discharged and treated to remove oxidation reaction inhibitors therefrom, before either being returned to the same reactor to repeat the oxidation reaction (in the single reactor embodiment of the present invention), or being delivered to a next sequential reactor (in a multiple-reaction embodiment hereof), for a repetition of the oxidation process, but with a much lower level of oxidation reaction inhibitors present in the reactor.

Thus, the inventive CHP production process is conducted in a continual cycle of removing oxidation products, treating them to remove reaction inhibitors and repeating the oxidation reactions with steadily decreasing levels of oxidation reaction inhibitors continues until a predetermined required CHP concentration is achieved by the process. Moreover, advantageously, in the preferred embodiment of the invention, the novel process utilizes various techniques to accelerate the oxidation reaction in at least one of the reactors, enabling the reaction to take place at a lower temperature, which both improves process safety, and improves selectivity, at least in part by reducing the formation of undesirable oxidation by-products that would otherwise inhibit the reaction. As a result, the inventive process is capable of virtually eliminating, or at least significantly reducing, the negative effect of pre-existing reaction inhibitors in the cumene delivered to the process, as well as substantially reducing formation of, and/or removing, reaction by-product inhibitors.

The novel oxidation process may be conducted in a series of two or more sequential reactors (e.g. 2 to 6) to achieve a required commercial CHP concentration (e.g., about 19-30 wt. %) at an outlet of the last reactor. In an alternate embodiment of the present invention, a single reactor may be utilized to conduct the novel oxidation process, for example, until a required commercial CHP concentration (e.g., about 19-30 wt. %) is achieved at the outlet of the reactor. Of course, the use of multiple reactors is preferable to a single reactor. However, a single reactor may be very useful in cases of limited resources, or during plant revamp implementations where equipment space is limited.

In each case, it is highly preferable (but not absolutely necessary) that each of the reactors used in connection with the inventive process (whether a single reactor or a series of sequential reactors are utilized) is provided with at least one airlift-type tray, and preferably with at least two airlift-type trays—at least one positioned in the bottom portion of the reactor, and at least one positioned above a center of the vertical axis of the reactor, such that when the process is conducted, the lower airlift-type tray fractures air bubbles that are formed in the vicinity thereof, and that impact the tray. The fractured bubbles are beneficial because they are smaller in size and thus of greater numbers that conventional air bubbles, creating a much larger and more evenly dispersed oxygen contact area for reacting with the organic phase, especially when the fractured bubbles rise from the at least one lower airlift-type tray, to the at least one higher airlift-type tray, such that the cumene oxidation reaction occurs at the expanded and more evenly dispersed air bubble—liquid interface. Advantageously, the resulting cumene oxidation reaction occurs significantly faster, with higher selectivity, and at a lower temperature. The lower temperature of the reaction is particularly beneficial as it reduces the formation of undesirable reaction inhibiting byproducts during oxidation.

At the same time, the trays can serve to discharge a part of the oxidation products to a stage of treatment of cumene oxidation products from process inhibitors, for example, such as sulfur-containing products, organic acids, phenol, and the like. This configuration advantageously allows maintenance, inside the reactors, of the required minimal concentration of formic and benzoic acids which lead to formation of an inhibitor (i.e. phenol) that decreases process selectivity. The discharged part of the products flows from the reactor through a tray zone, where a downward product stream is substantially free of air bubbles. In the inventive embodiment where a series of reactors is used, the products can be directed to treatment from an airlift tray, and/or from the bottom, or the top of the reactor.

When a specific desired CHP concentration is achieved in a process reactor, oxidation products are discharged from a reaction zone, and are then treated in a mixing device with aqueous ammonia or water to remove organic acids (formic acid, benzoic acid, etc.), and to remove phenol (which is an inhibitor of oxidation reaction), as well as other reaction inhibitors, from the oxidation products. At least a portion of the treated product flow is then forwarded into the next reactor, in case when a series of reactors is used, or, when a one-reactor configuration is used, at least a portion of the flow is returned to the same reactor. But in all embodiments of the present invention, the product is at least once treated with water or aqueous base solution (such as ammonia, NaOH, or ammonia and NaoH together), directed to a vessel for separation of aqueous phase from organic products, and then, in case of a reactor series embodiment, anhydrous organic products are forwarded to the next reactor of the series to enable continued cumene oxidation until the required CHP concentration is achieved.

Similar treatment of cumene oxidation products (i.e., discharging from the reaction zone, treatment in a mixing device with aqueous ammonia or water, removal of the liquid phase from organic products, etc.), is carried out after each reactor in the series (or in only a portion of the series of reactors, depending on the actual cumene conversion level, and therefore, on the level of organic acids and phenol concentration in cumene oxidation products).

While the process of the present invention is relatively flexible with regard to operating reactor temperature ranges, preferably, in a single reactor the reactor temperature is preferably maintained at about 85° C. to about 125° C., and when a series of reactors is used, the temperature in sequential reactors decreases towards the last reactor of the series. The temperatures in the series reactors may range from about 115° C. (upper limit) to about 85° C. (lower limit), and the specific required temperature in each individual reactor in the series within the desired temperature range is determined by the required productivity of the reactors, i.e., a CHP production rate from 1 m$^3$ of that reactors volume. In the above-described preferred embodiment of the invention, the fact that the reactor or reactors utilized for the oxidation process each comprises at least two airlift-type trays enables the cumene oxidation reaction to be conducted at a lower temperature than would be otherwise possible, without appreciable slowdown of reaction and without a substantial loss in selectivity.

Certainly the process can be conducted under conditions in which temperature ranges fall outside the above-recommended range. However, research has shown that when reactor temperature exceeds about 115° C., the reactor productivity increases, but at a cost of a drop in process selectivity. On the other hand, if reactor temperature falls below about 85° C., there is a positive effect on selectivity, but a larger reactor would be required for proper completion of the reaction, therefore greatly increasing capital expenditures for process implementation.

In another embodiment of the present invention, devices for maintaining air-free regions in a reactor (such as the above-described airlift-type trays) are installed in one or more, but not in all reactors, to improve the cumene oxidation reaction, and to increase process performance, as well as selectivity. For example in a multiple-reactor embodiment of the process, it may not be practical to install airlift-type trays in a last of the reactors.

Reactor pressure can range from 1 atm. to 7 atm. and is adjusted based on the specific CHP productivity value per 1 m$^3$ of reactor volume, as required by the process administrator, or based on the CHP formation rate within the range of 2.5% to 1.5% per hour. Pressure range at the acid washout and aqueous phase removal stage also ranges from about 1 atm. to about 7 atm. and is controlled by the reactor pressure.

After leaving a reactor, the oxidate may be treated with aqueous base (such as $NH_3$) solution, for example having a $NH_3$ concentration value from about 0.1 wt. % to about 20 wt. %, and the $NH_3$ concentration value and the quantity added to the reactors is determined by the quantity of the developing organic acids, i.e. both concentration and quantity values depend on the cumene conversion degree, reactor temperatures, and on whether or not the reactors are installed in series, or a single reactor is used.

In an alternate embodiment of the invention, in a series reactor process implementation, the oxidate may be treated with an aqueous base solution after leaving only some of the reactors (for example, in a four reactor series, the oxidate may be treated after leaving the first and the fourth reactors). Similarly, the manner in which the contact between the oxidate and the aqueous base is conducted, and then the manner in which the organic and aqueous phases are separated, may also be selected as a matter of design choice—for example, a mixer can be used to improve contact between the oxidate and the aqueous base solution, while a settler, coalescer, or cyclone may be used to separate the phases.

During cumene oxidation, the oxygen content in off-gases released in the reaction is preferably maintained within the range of about 2 vol. % to about 8 vol. %, and carefully adjusted to avoid the limits of explosive concentrations.

After the cumene oxidation end product has gone through the final stage of organic acids neutralization (for example, with $NH_3$) and washout with water, it is forwarded to a CHP concentration stage to produce technical CHP containing from about 60 wt. % to about 95 wt. % of the target product (i.e., CHP), which is thereafter directed to acid-catalyzed CHP cleavage to phenol, acetone, and alphamethylstyrene (a valuable by-product).

Recycle cumene streams coming out from off-gas condensation stage and CHP concentration stage are treated in a manner well known in the art (e.g., adsorption, de-sorption, drying, etc.).

The various features of novelty which characterize the invention are pointed out with particularity in the claims appended to and forming a part of this specification. For a better understanding of the invention, its operating advantages and specific objects obtained by its use, reference should be had to the accompanying drawings and descriptive matter in which there is illustrated and described a preferred embodiment of the invention.

BRIEF DESCRIPTION OF THE DRAWINGS

In the drawings, wherein like reference characters denote corresponding or similar elements throughout the figure.

DETAILED DESCRIPTION OF PREFERRED EMBODIMENTS

Figure 1:
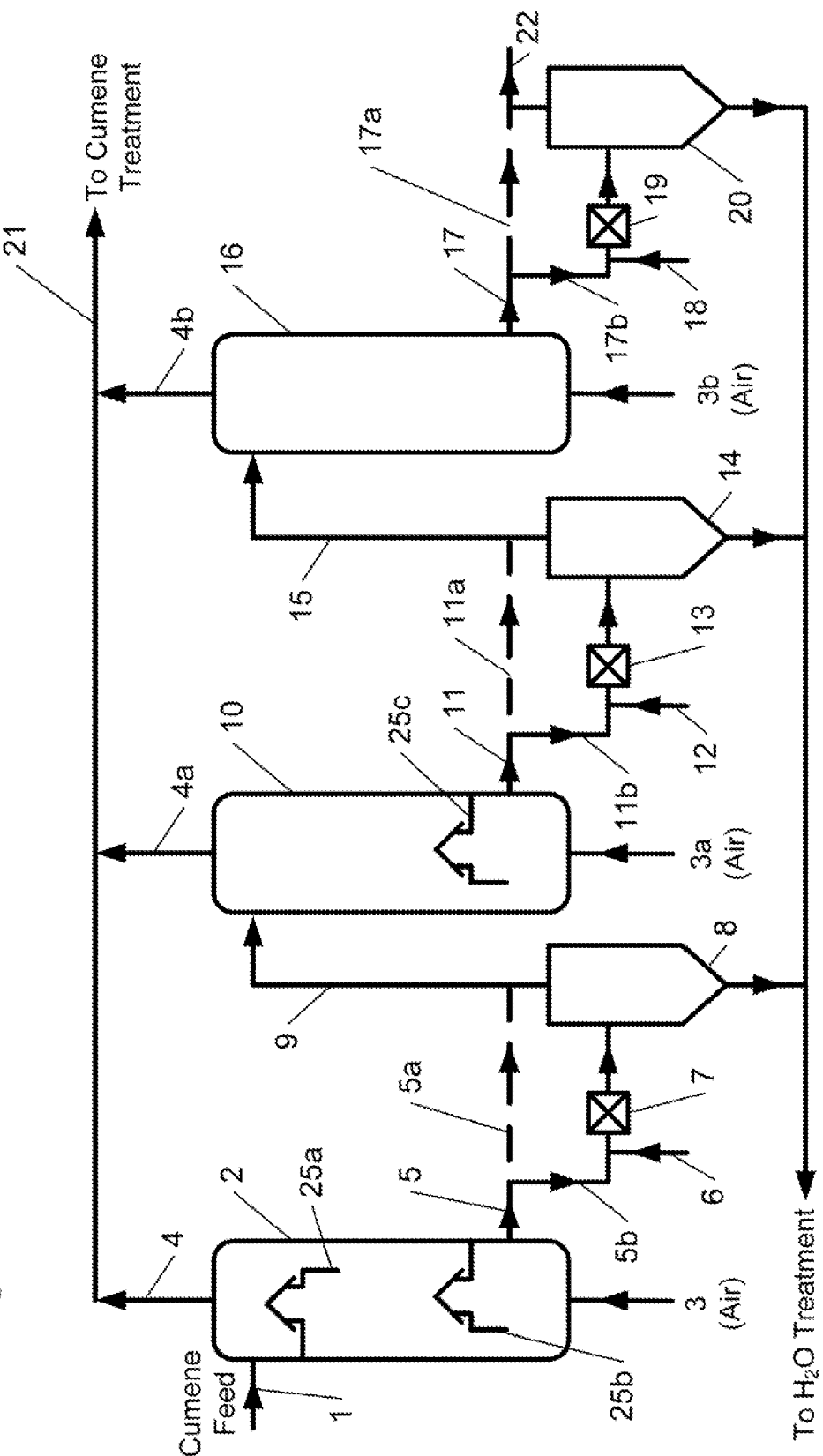
FIG. 1 is a schematic diagram of a first embodiment of the inventive process of production of cumene hydroperoxide.

The present invention is aimed at eliminating the disadvantages of previously known CHP oxidation processes and at improving the safety, conditions, of a cumene to CHP oxidation process, and for lowering the incoming raw material cumene quality requirements, thereby lowering the process expense. In accordance with the present invention, high process selectivity and high productivity with regard to desired product are also achieved.

The process of the present invention is intended to operate as part of a complete process for production of CHP. Accordingly, certain well-known process stages, such as AMS hydrogenation, that may occur before, during, and after the inventive process are referred to below but not described in detail. Furthermore, it should be understood that in describing embodiments of the process of the present invention, varying types, quantities, and concentrations of products, inhibitors, impurities and agents are used by way of illustrative examples only and are not intended to serve as limitations for the inventive process other than as recited in the appended claims.

The inventive process utilizes one or more sequential reactors to conduct cumene oxidation while removing and reducing the formation of undesirable reaction-inhibiting by-products. In each reactor (or during each repeated reaction cycle if a single reactor is utilized), CHP concentration is monitored during the oxidation reaction, and, when a predetermined threshold CHP concentration is reached, at least a portion of the oxidation products are discharged and treated to remove oxidation reaction inhibitors therefrom, before either being returned to the same reactor to repeat the oxidation reaction (in the single reactor embodiment of the present invention), or being delivered to a next sequential reactor (in a multiple-reaction embodiment hereof), for a repetition of the oxidation process, but with a much lower level of oxidation reaction inhibitors present in the reactor.

Thus, the inventive CHP production process is conducted in a continual cycle of removing oxidation products, treating them to constantly remove reaction inhibitors and repeating the oxidation reactions with steadily decreasing levels of oxidation reaction inhibitors continues until a predetermined required CHP concentration is achieved by the process. Moreover, advantageously, in the preferred embodiment of the invention, the novel process utilizes various techniques to accelerate the oxidation reaction in at least one of the reactors, enabling the reaction to take place at a lower temperature, which both improves process safety, and improves selectivity, at least in part by reducing the formation of undesirable oxidation by-products that would otherwise inhibit the reaction. As a result, the inventive process is capable of virtually eliminating, or at least significantly reducing, the negative effect of pre-existing reaction inhibitors in the cumene delivered to the process, as well as substantially reducing formation of, and/or removing, reaction by-product inhibitors.

In accordance with the present invention, a heterophase process of cumene oxidation by air oxygen is conducted in a series of sequential reactors, or in a single reactor (in an alternate embodiment of the present invention). In each case, it is highly preferable, but not absolutely necessary, that each of the reactors used in connection with the inventive process (whether a single reactor or a series of sequential reactors are utilized) is provided with at least one airlift-type tray, and preferably with at least two airlift-type trays—at least one positioned in the bottom portion of the reactor, and (if more than one tray is utilized), at least one positioned above a center of the vertical axis of the reactor, such that when the process is conducted, the lower airlift-type tray fractures air bubbles that are formed in the vicinity thereof, and that impact the tray.

The continually fractured bubbles are beneficial because they are smaller in size and thus of greater numbers that conventional air bubbles, creating a much larger oxygen contact area of a more uniform dispersal profile for reacting with the organic phase, then unfractured air bubbles, especially when the fractured bubbles rise from the at least one lower airlift-type tray, to the at least one higher airlift-type tray, such that the cumene oxidation reaction occurs at the expanded and more evenly dispersed air bubble—liquid interface. Furthermore, the smaller size of the fractured air bubbles means that they rise slower through the reactor, thus increasing their residence time in the reactor and the duration of their contact with the organic phase.

Advantageously, the resulting cumene oxidation reaction occurs significantly faster, with higher selectivity, and at a lower temperature. In another embodiment of the present invention, devices for maintaining air-free regions in a reactor (such as the above-described airlift-type trays) are installed in one or more, but not in all reactors, to improve the cumene oxidation reaction, and to increase process performance, as well as selectivity. For example in a multiple-reactor embodiment of the process, it may not be practical to install airlift-type trays in a last of the reactors.

Referring now to FIG. 1, a first embodiment of a cumene oxidation process of the present invention is shown as implemented, by way of example, in a series of (in this case, three) sequential reactors. It should be noted that more or less reactors can be utilized as a matter of design choice without departing from the spirit of the invention. An oxidation feed (stream (1)) is directed to a first reactor (2) of the series. The stream 1 is preferably directed from a stage of oxidation feed preparation, and may include a mixture of fresh cumene and recycle cumene streams from at least one or more of the following:

a CHP concentration stage,
off-gas condensation stage,
off-gas adsorptive treatment stage,
and AMS hydrogenation stage
target AMS production stage from.

An air stream (3) is also injected into reactor (2). The temperature in the first reactor (2) is preferably maintained at a range between about 90° C. to about 125° C., the pressure is preferably maintained within a range of about 1 atm. to about 7 atm. Cumene conversion degree in the first reactor is kept at about 5 to about 10 mole %. Cumene oxidation off-gases (stream (4)) containing cumene and minor amount of organic acids, are condensed to remove major amount of cumene from the off-gas.

Off-gas condensate, i.e. recycle cumene stream, is returned to the feed preparation stage as a stream (21). After condensation, the oxidation off-gases are forwarded to treatment. Cumene oxidation products (stream (5b)) are taken off from the reactor (2) to treatment with an aqueous base solution (e.g., aqueous ammonia, or equivalent thereof) to remove organic acids and, at least partially, phenol, from the oxidate. Cumene oxidation products (stream (5b)), as well as aqueous ammonia (stream (6)) are then directed into a mixer (7). By way of example, the aqueous phase may include, but is not limited to at least one or more of the following, individually, or in conjunction with one another, a sufficient quantity of sodium carbonate to facilitate separation of said organic phase from the aqueous phase, a quantity of sodium carbonate that is below a limit of water solubility thereof, a caustic NaOH solution, and/or an ammonia solution.

In the preferred embodiment of the invention, while a single airlift-type tray may be utilized in accordance with the present invention, preferably at least two tray devices (25a), (25b), used to generate air-free zones in the reactor (2), preferably airlift-type trays, are installed in the reactor (2), with at least one of the airlift-type trays (25a) being above a center of the vertical axis of the reactor (2), and at least one of the airlift-type trays (25b) being in the bottom portion of the reactor (2). The airlift-type trays (25a), (25b), serve to break up the air bubbles formed during the oxidation reaction, creating with the larger number of smaller air bubbles, a much larger oxygen contact area, with a more uniform dispersal profile, and a longer reactor residence time for reacting with the organic phase, which in turn causes the cumene oxidation reaction to occur significantly faster and at a lower temperature, which results in higher process selectivity and improved process safety.

Cumene oxidation products (stream (5b) can be taken off to treatment from the airlift tray (25b), as well as from the bottom, or from the top of the reactor (2). The quantity and concentration of aqueous base (e.g., ammonia) utilized for cumene oxidation product treatment must be maintained at such level so that the oxidation product pH value does not fall outside the range of between about 5 to about 7, because the increase of pH value above 7, or decrease of pH value below 5, decreases process selectivity (this was shown by experiments performed during development of the inventive process).

After washout and water separation in a phase separator (8) (which may be a settler, coalescer, cyclone, or equivalent thereof), cumene oxidation products (stream (9)) are directed to a reactor (10). Aqueous alkali phase from the phase separator (8) is forwarded to a downstream CHP cleavage product neutralization stage (shown as "to treatment $H_2O$" in FIG. 1). An air stream (3a) is also injected into the second reactor (10). The second reactor (10) temperature is kept at about 90° C. to about 120° C., while pressure is maintained from about 1 atm. to about 7 atm. Cumene conversion degree in the second reactor (10) is maintained at about 10 to about 15 mole %. Cumene oxidation off-gases (stream (4a)) containing cumene and insignificant amount of organic acids are condensed to remove major amount of cumene, and then are forwarded to treatment.

Cumene oxidation products (stream (11b)) and aqueous base solution (stream (12)) are directed into a mixer (13). As noted above, with respect to reactor (2), reactor (10) may also be equipped with at least one air-free zones, such as generated by an airlift-type tray (25c). By way of example only, the reactor (10) is shown with a single airlift-type tray (25c), although a greater quantity of airlift-type trays can be readily utilized (or, optionally, the reactor (10) may be configured without an airlift-type tray). Cumene oxidation products (stream (11b)) can be taken off to treatment from the airlift-type tray (25c), as well as from the bottom, or from the top of the reactor (10). The quantity and concentration of aqueous base (e.g., ammonia) utilized for cumene oxidation product treatment must be maintained at such level so that the oxidation product pH value does not fall outside the range of between about 5 to about 7.

After washout and water removal in a phase separator (14) (which may be similar to the phase separator (8)), cumene oxidation products (stream (15)) are directed to a third reactor (16). Aqueous alkali phase from phase separator (14) is then directed to treatment. An air stream (3b) is also injected into the third reactor (16). The third series reactor (16) temperature is preferably maintained at about 90° C. to about 110° C., and pressure is preferably maintained from about 1 atm. to about 7 atm. Cumene conversion degree in the third reactor (16) is preferably kept at about 15 to about 20 mole %.

Cumene oxidation off-gases (stream (4b)) containing cumene and minor amount of organic acids are condensed to remove major amount of cumene and then are forwarded to treatment. Cumene oxidation products (stream (17b)) as well as aqueous base solution (stream (18)) are directed into a mixer (19). By way of example, reactor (16) is shown without any airlift-type trays. However, as noted above, one of more airlift-type trays may be readily provided and used in reactor (16) as a matter of design choice. Cumene oxidation products (stream (17b)) can be taken off to treatment from the bottom, or from the top of the reactor (16). The quantity and concentration of aqueous base (e.g., ammonia) utilized for cumene oxidation product treatment must be maintained at such level so that the oxidation product pH value does not exceed about 7.

After washout and water removal in a phase separator (20), cumene oxidation products (stream (22)) are forwarded to the following reactors of the series (if more than three reactors are used), or to the CHP concentration stage. Aqueous alkali phase from apparatus (20) is directed to the downstream cumene hydroperoxide cleavage product neutralization stage.

In an alternate embodiment of the inventive process of FIG. 1, in a series reactor process implementation, the oxidate may be treated with the aqueous base solution (e.g. streams (6), (12), and (18)) after leaving only some of the reactors (for example, the oxidate may be treated after leaving reactor (2) and reactor (16), but not after leaving reactor (10) the first and the fourth reactors, but not after leaving the second and the third). In such a case, a mixer and phase concentrator are not necessary after a reactor where the oxidate is untreated—instead the oxidate directly flows into the next reactor in the series. These optional direct connections are shown as streams (5a), (11a), and (17a).

Similarly, the manner in which the contact between the oxidate and the aqueous base is conducted, and then the manner in which the organic and aqueous phases are separated, may also be selected as a matter of design choice—for example, while a mixer can be used to improve contact between the oxidate and the aqueous base solution, other forms of contact can be achieved with different devices. As noted above, the bubbles generated by utilization of at least two airlift-type trays (25a) to (25c) in at least one of the reactors (2), (10), and/or (16) provide an optimized technique of achieving contact between oxygen-filled bubbles and the liquid phase in the reactor.

Figure 2:
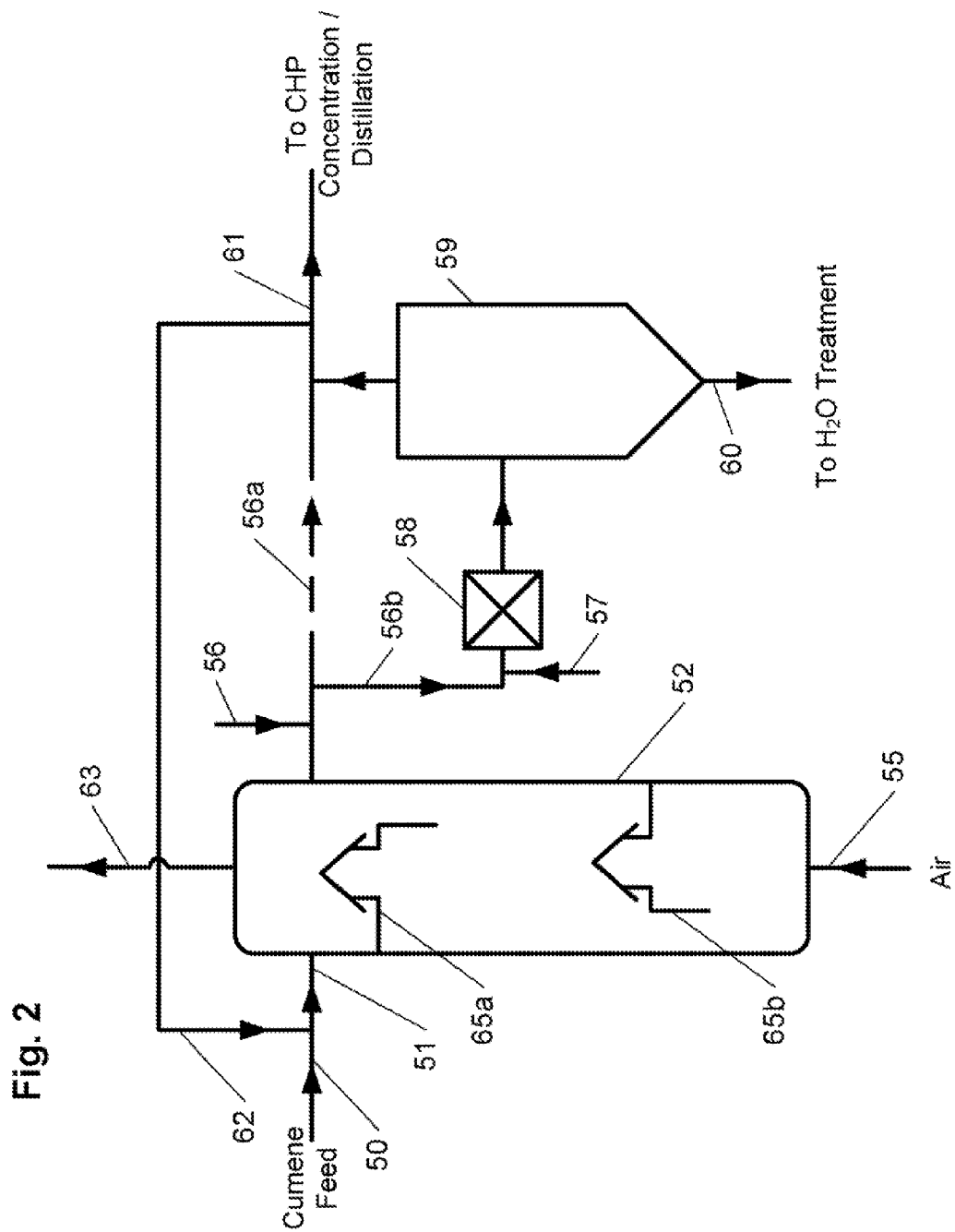
FIG. 2 is a schematic diagram of a second embodiment of the inventive process of production of cumene hydroperoxide.

Referring now to FIG. 2, a second embodiment of the present invention is shown demonstrating the novel cumene oxidation process conducted in a single reactor. This embodiment is particularly advantageous for retrofit implementation, where there may not be enough space for a series of reactors.

An oxidation feed (stream (50)) is directed to a reactor (52). The stream (50) is preferably directed from a stage of oxidation feed preparation, and may include a mixture of fresh cumene and recycle cumene streams from at least one or more of the following:
 a CHP concentration stage,
 off-gas condensation stage,
 off-gas adsorptive treatment stage,
 and AMS hydrogenation stage
 target AMS production stage from.

As noted below, at least a portion of cumene oxidation products of the novel process, are also returned as a stream (62) and join (and/or mixed with) stream (50) to form a stream (51).

An air stream (55) may be injected into reactor (52). The temperature in the reactor (52) is preferably maintained at a range between about 90° C. to about 125° C., the pressure is preferably maintained within a range of about 1 atm. to about 7 atm. Cumene conversion degree in the first reactor is kept at about 17 to about 10 mole %. Cumene oxidation off-gases (stream (63)) containing cumene and minor amount of organic acids, are condensed to remove major amount of cumene from the off-gas.

Off-gas condensate, i.e. recycle cumene stream, is returned to the feed preparation stage as a stream (63). After condensation, the oxidation off-gases are forwarded to treatment. Cumene oxidation products (stream (56*b*)) are taken off from the reactor (52) to treatment with an aqueous base solution (e.g., aqueous ammonia, or equivalent thereof) to remove organic acids and, at least partially, phenol, from the oxidate. Cumene oxidation products (stream (56*b*)), as well as aqueous base solution (stream (57)) are then directed into a mixer (58). The optional direct connection is shown as stream (56*a*).

In one embodiment of the invention, tray devices used to generate air-free zones in the reactor (52) (i.e., airlift-type trays (65*a*), (65*b*)) are installed in the reactor (52). Cumene oxidation products (stream (56*b*) can be taken off to treatment from an airlift-type tray (65*a*), as well as from the bottom, or from the top of the reactor (52). The quantity and concentration of aqueous base (e.g., ammonia, etc.) utilized for cumene oxidation product treatment must be maintained at such level so that the oxidation product pH value does not exceed about 7, because the increase of pH value decreases process selectivity (this was shown by experiments performed during development of the inventive process).

The quantity and concentration of ammonia at cumene oxidation products treatment must be kept at such level so that the oxidation product pH value does not fall outside the range of between about 5 to about 7. After washout and water removal in a phase separator (59) (which may be a settler, coalescer, cyclone, or equivalent thereof) cumene oxidation products (stream (62)) are partly returned to the reactor (52) and mixed with stream (50) to form stream (51). The remaining cumene oxidation products (stream 61) are directed to the CHP concentration stage. The mass ratio of the oxidate returned to the reactor to the part directed to CHP concentration stage makes up approximately (0.1 to 0.6):1. Aqueous alkali phase (stream (60) from phase separator 59 is taken off to the downstream CHP cleavage product neutralization stage.

The inventive process (as illustrated by embodiments of FIGS. 1 and 2), differs from the previously known multi-stage oxidation techniques by at least the following features:

1. The cumene to CHP oxidation process is conducted directly in a reactor series or in one reactor, and includes multiple repeated stages of cumene oxidation product treatment with aqueous base solution (such as caustic solution (NaOH), ammonia solution, sodium carbonate, or any combination thereof etc.), to remove organic acids and to partially remove phenol;
2. At least one airlift-type tray may be utilized in at least one of the process reactors to accelerate the cumene oxidation process, while increasing process selectivity and allowing the oxidation process to be conducted at lower temperatures;
3. The stage of cumene oxidation product treatment is carried out in a specially installed vessel; and to enlarge the contact of phases, the cumene oxidation products are mixed with aqueous base in a mixer;
4. All, or only a portion of, the products from the single reactor or a reactor series can be treated. The mass ratio of the treated products to non-treated portion is preferably maintained at (1 to 0.5): 0.001;
5. Ammonia content at the stage of cumene oxidation product treatment must be kept at such level so that the oxidation product pH value does not exceed about 7; and
6. Water, which inhibits the process and decreases selectivity, is removed from the products which are subjected to the oxidation.

In the process of the present invention, high productivity (CHP formation rate is 2.5% to 1.5% per hour) is obtained by keeping high selectivity at about 95 mol. % and cumene conversion at about 21 to 22 about mole % in case of series reactors (embodiment of FIG. 1), and at about 93 mol. % and cumene conversion at 17 to 19 mol. %, when non-series type reactors are used (embodiment of FIG. 2). The above-described advantages and features of the present invention are demonstrated by Examples 2 through 6 (see also Table 2, Cumene Oxidation Summary), while Example 1 illustrates a conventional prior art process for comparative purposes.

It should be noted that specific reactor temperature ranges, the number of series reactors used, and other implementation parameters given in the Examples are illustrative only and are not meant to restrict or limit the invention. The improved process of cumene oxidation is applicable in any standard process of non-emulsion cumene oxidation.

The comparative laboratory simulations of cumene oxidation in the conventional process (Example 1) and in the inventive process (Examples 2 through 6) were made with the use of 99.9% purity degree cumene. The laboratory unit for studying the cumene oxidation process consisted of a glass reactor of the height 300 mm and the inner diameter 22 mm and a continuous feeding block—each reactor was supplied with at least two airlift-type trays. A temperature sensor thermocouple, is installed to measure the temperature along the reactor height. The reactor temperature was controlled and stabilized by the temperature controller PROTERM-100. In the bottom of the reactor, a glass filter acting as an air distributor was installed. The pressure control was actuated by a pressure meter installed at the reactor outlet. The air stream rate was measured by a flow meter precalibrated according to a gas meter. The continuous feeding block consists of a joined feed vessel and glass burette to measure the feed rate and a micro dozing pump. In the top of the reactor vapor-gas space was preferably maintained and liquid level in the reactor was controlled visually.

Oxidation off-gases coming out from the reactor were condensed in knockouts, which were cooled to −5° C. Oxygen concentration in oxidation off-gases was controlled by an oxygen gas analyzer. Oxygen concentration in off-gases was kept at 5-6 mole %. Oxidation products were taken off from the reactor and were analyzed.

EXAMPLE 1

Prior Art Conventional Process

The feed for the cumene oxidation process was prepared by mixing fresh cumene produced by a zeolite-catalyzed method and recycle cumene from the CHP concentration stage at a ratio of 1:3. The feed was treated with 3 wt. % NaOH solution, a mixture of 10 wt. % aqueous sodium carbonate which contained 0.7 wt. % of sodium bicarbonate, and 5 wt. % aqueous ammonia at the equimolar ratio of ammonia to sodium bicarbonate (solution A). The feed contained 99.06 wt. % cumene, 0.043 wt. % AP, 0.17 wt. % DMBA, and 0.72 wt. % CHP. The feed to the reactors was at a rate of 50 mL/hr, the residence time of the oxidate in each reactor was 2.0 hours. At the first process step (represented by initial three reactors of a six reactor series), a mixture of 0.7 wt. % aqueous sodium carbonate and solution A at a weight ratio of 1:1 was added to the reactors to neutralize organic acids that have been formed. At the second process step (represented by last three reactors), 0.7 wt. % aqueous sodium carbonate and fresh water were added to the reactors. The results obtained are summarized in Table 1.

TABLE 1

Cumene Oxidation Results from Prior Art Example 1

| Operating parameters | Step 1 | | | Step 2 | | |
|---|---|---|---|---|---|---|
| | Reactor # | | | | | |
| | I | II | III | IV | V | VI |
| Temperature, °C. | 107.2 | 102.7 | 99 | 95.5 | 93 | 92 |
| Pressure, above atm | 5 | 5 | 5 | 5 | 5 | 5 |
| Outlet CHP concentration, % wt. | 6.3 | 10.7 | 15.7 | 19.4 | 22.6 | 25.9 |
| CHP Formation rate, % per hour | 2.8 | 2.2 | 2.5 | 1.85 | 1.6 | 1.65 |
| Selectivity over Reactors, mole % | 93.3 | 94.0 | 94.2 | 93.9 | 93.8 | 93.7 |
| Total Process Selectivity, mole % | 93.8 | 94.2 | 94.5 | 94.0 | 93.9 | 93.9 |
| Total Cumene Conversion, mole % | 5.3 | 9.0 | 13.2 | 16.3 | 19.0 | 21.8 |

EXAMPLE 2

Cumene oxidation by the first embodiment of the inventive process of FIG. 1 was conducted in a series system consisting of four reactors, each having at least two airlift-type trays installed therein. Fresh cumene produced by zeolite-catalyzed method and recycle cumene streams from the cumene condensation, CHP concentration, α-methylstyrene (AMS) hydrogenation steps treated by conventional method were used as the feed. The feed contained 0.93 wt. % CHP, 0.105 wt. % DMBA, 0.017 wt. % AP, no dicymyl peroxide (DCP), and 0.022 wt. % AMS. The feed flowed to the reactors at a rate of 40 mL/hr and the residence time of the oxidate in each reactor was 2.6 hours. The temperature in the first reactor was kept at 104.5° C. in the second reactor 101° C., in the third reactor at 96° C., and in the fourth reactor at 94° C. The oxidation products after the first, second, and third series reactors before being fed to the subsequent reactor were treated with aqueous ammonia solution to pH=7. The aqueous phase and organic phase were settled out in a separatory funnel for 20 minutes. The organic phase was filtered using silicone treated filter paper (1 PS Whatman) to remove the traces of undissolved water. The CHP formation rate was 2.4% to 2.5% per hour in the first and second reactors and 2.27% to 1.9% per hour in the third and fourth reactors. The total process selectivity was 95.1 mole % at a cumene conversion of 20.2 mole %. The oxidation process parameters of this example are summarized in Table 2.

EXAMPLE 3

The oxidation was conducted in the same manner as in Example 2, (i.e., utilizing reactors each with at least two airlift-type trays installed therein, etc.) except that cumene was represented by cumene produced with the use of aluminum chloride catalyst with a sulfur content of 1-3 ppm. The feed contained 1.11 wt. % CHP, 0.078 wt. % DMBA, 0.014 wt. % AP, no DCP, and 0.0207 wt. % AMS. The feed flew to the reactors at a rate of 40 mL/hr, the residence time of the oxidate in each reactor was 2.6 hours. The temperature in the first reactor was kept at 106° C., in the second reactor at 102° C., in the third reactor at 97° C., and in the fourth reactor at 95° C. The oxidation products after the first, second, and third series reactors before being fed to the subsequent reactor were treated with aqueous ammonia solution to pH=7. The aqueous phase and organic phase were settled out in a separatory funnel for 20 minutes. The organic phase was filtered using silicone treated filter paper (1 PS Whatman) to remove the traces of undissolved water. The CHP formation rate was 2.5% to 2.4% per hour in the first and second reactors and 1.8% to 1.9% per hour in the third and fourth reactors. The total process selectivity was 95.0 mole % at a cumene conversion of 19.6 mole %. The oxidation process parameters of this example are summarized in Table 2.

EXAMPLE 4

The oxidation was conducted in the same manner as in Example 3 (i.e., utilizing reactors each with at least two airlift-type trays installed therein, etc.), except that the oxidate treatment with aqueous ammonia solution was performed after the third reactor only. The aqueous phase and organic phase were settled out in a separatory funnel for 20 minutes. The organic phase was filtered using silicone treated fitter paper (1 PS Whatman) to remove the traces of undissolved water. The feed contained 1.20 wt. % CHP, 0.095 wt. % DMBA, 0.018 wt. % AP, no DCP, and 0.021 wt. % AMS. The temperature in the first reactor was kept at 104° C., in the second reactor at 100.5° C., in the third reactor at 99.5° C. and in the fourth reactor at 99° C. The CHP formation rate was 2.6% to 2.2% per hour in the first and second reactors and 1.5% to 2.5% per hour in the third and fourth reactors. The total process selectivity was 95.2 mote % at a cumene conversion of 20.1 mole %. The oxidation process parameters of this example are summarized in Table 2.

EXAMPLE 5

The oxidation was conducted in the same manner as in Example 3 (i.e., utilizing reactors each with at least two airlift-type trays installed therein etc.), except that the first reactor feed lacked the stream from AMS hydrogenation stage. The feed contained 1.10 wt. % CHP, 0.087 wt. % DMBA, 0.016 wt. % AP, no DCP, and no AMS. The temperature in the first reactor was kept at 105° C., in the second reactor at 101° C., in the third reactor at 97° C. and in the fourth reactor 95° C. The total process selectivity was 95.2 mole % at a cumene conversion of 20 mole %. The oxidation process parameters of this example are summarized in Table 2.

TABLE 2

Cumene Oxidation Summary from Examples 2-5

| Example # | 2 | | | | 3 | | | | 4 | | | | 5 | | | |
|---|---|---|---|---|---|---|---|---|---|---|---|---|---|---|---|---|
| Reactor # | I | II | III | IV | I | II | III | IV | I | II | III | IV | I | II | III | IV |
| Temperature, ° C. | 104.5 | 101 | 96 | 94 | 106 | 102 | 97 | 95 | 104 | 100.5 | 99.5 | 99 | 105 | 101 | 97 | 95 |
| Outlet CHP Concentration, % wt. | 7.2 | 13.7 | 19.4 | 24.3 | 7.6 | 13.9 | 18.6 | 23.5 | 7.7 | 13.5 | 17.5 | 24.1 | 8.5 | 13.9 | 18.5 | 23.7 |
| CHP Formation Rate, % per hour | 2.4 | 2.5 | 2.2 | 1.9 | 2.5 | 2.4 | 1.8 | 1.9 | 2.6 | 2.2 | 1.5 | 2.5 | 2.9 | 2.1 | 1.8 | 2.0 |
| Selectivity over Reactors, mole % | 96.4 | 95.6 | 95.3 | 94.9 | 95.7 | 95.4 | 95.2 | 94.8 | 95.4 | 95.4 | 95.5 | 94.9 | 95.8 | 95.5 | 95.3 | 94.9 |
| Total Process Selectivity, mole % | 97.0 | 95.8 | 95.4 | 95.1 | 96.8 | 95.9 | 95.6 | 95.2 | 96.4 | 96.0 | 95.9 | 95.0 | 96.8 | 96.0 | 95.8 | 95.3 |
| Total Cumene Conversion, mole % | 5.8 | 11.3 | 16.0 | 20.2 | 6.2 | 11.6 | 15.4 | 19.6 | 6.4 | 11.2 | 14.5 | 20.1 | 6.1 | 11.5 | 15.4 | 19.9 |

EXAMPLE 6

The oxidation was conducted in the same manner as in Example 3 (i.e., utilizing reactors each with at least two airlift-type trays installed therein, etc.), except that the process was conducted in a single reactor rather than a series. The feed contained 3.70 wt. % CHP, 0.264 wt. % DMBA, 0.046 wt. % AP, 0.023 wt. % DCP, and 0.0120 wt. % AMS. The reactor temperature was kept at 108° C. The residence time was 3.8 hours. The total process selectivity was 92 mole % at a cumene conversion of 17.5 mole %.

Thus, while there have shown and described and pointed out fundamental novel features of the invention as applied to preferred embodiments thereof it will be understood that various omissions and substitutions and changes in the is form and details of the devices and methods illustrated, and in their operations may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

We claim:

1. A continuous method for producing cumene hydroperoxide (CHP) through cumene oxidation by air oxygen in at least one sequential reactor, comprising the steps of
   (a) providing said at least one sequential reactor, at least one reactor thereof comprising at least one airlift-type tray and at least one air-free area;
   (b) conducting the cumene oxidation reaction in said at least one sequential reactor, in one of said at least one sequential reactor until a predetermined threshold CHP concentration is reached;
   (c) during said step (b), fracturing a first plurality of air bubbles formed during the cumene oxidation reaction having a first oxygen contact area, by said at least one airlift-type tray, to generate a greater plurality of smaller air bubbles having a second oxygen contact area greater than said first oxygen contact area and having a longer residence time in said at least one sequential reactor, thereby accelerating the cumene oxidation reaction;
   (d) discharging an oxidate, resulting from said accelerated cumene oxidation reaction, from said at least one of said air-free areas of said at least one sequential reactor;
   (e) selectively causing contact between said oxidate and an aqueous base solution, to remove at least one reaction inhibitor, such that after said contact, said oxidate comprises an aqueous phase and an organic phase, wherein said step (e) is performed at least once; and
   (f) selectively physically separating said aqueous phase from said organic phase and:
      (1) when said at least one sequential reactor comprises a single reactors recycling said organic phase to said single reactor to perform said steps (a) to (f) until a predetermined required CHP concentration is achieved, and
      (2) when said at least one sequential reactor comprises a plurality of sequential reactors, passing said organic phase to a next plural sequential reactor to perform said steps (a) to (f) until said predetermined required CHP concentration is achieved, and recycling said organic phase to a first of said plural sequential reactors when said step (a) has been performed in a east plural sequential reactor, and said predetermined required CHP concentration has not yet been achieved.

2. The method of claim 1, wherein said step (e) comprises the step of:
   (g) selectively treating at least a portion of said oxidate in a mixing device by said aqueous base solution, to remove said at least one reaction inhibitor, such that said oxidate comprises an aqueous phase and an organic phase.

3. The method of claim 1, further comprising the step of:
   (h) maintaining, after each performance of said step (e), a concentration of said organic acids in said oxidate at no more than about 10 ppm.

4. The method of claim 1, further comprising the step of:
   (i) maintaining, after each performance of said step (a) and before said step (e), a concentration of CHP within a range of about 7 wt. % to about 30 wt. %.

5. The method of claim 1, wherein said step (f) is performed using at least one of the following group of physical phase separation techniques: settling, utilizing a coalescer, and utilizing a cyclone.

6. The method of claim 1, wherein said aqueous phase comprises at a sufficient quantity of at least one of: a caustic solution, an ammonia solution, sodium carbonate, or any combination thereof to facilitate said separation of said organic phase from said aqueous phase.

7. The method of claim 1, wherein said at least one sequential reactor comprises a first zone having a lower quantity of air bubbles therein than in other portions of said at least one sequential reactor, and wherein said step (d) comprises the step of:
(j) discharging said oxidate from said first zone.

8. The method of claim 1 wherein said at least one sequential reactor comprises a single reactor, further comprising the step of:
(k) maintaining, during performance of said steps (a) to (e): a reactor temperature within a range of about 90 degrees C. to about 125 degrees C.

9. The method of claim 1, wherein said at least one sequential reactor comprises a plurality of sequential reactors, further comprising the step of:
(l) decreasing, during performance of said steps (a) to (e), a reactor temperature from a first plural sequential reactor to a last plural sequential reactor, white maintaining, during performance of said steps (a) to (e), a reactor temperature in each plural reactor within a range of about 85 degrees C. to about 115 degrees C.

10. The method of claim 1, wherein a first plurality of air bubbles is formed during said step (a), said first plural air bubbles, being of a first quantity, of a first dispersal profile, and of a first reactor residence time, and having a first oxygen contact area, and wherein said step (a) comprises the step of:
(m) fracturing, by said at least one airlift-type tray, of said plural air bubbles, to produce a plurality of fractured air bubbles of a second quantity, substantially greater than said first quantity, being of a second dispersal profile, more uniform than said first dispersal profile, and of a second reactor residence time greater than said first reactor residence time, and having a second oxygen contact area substantially greater than said first oxygen contact area, such that presence of said plural fractured bubbles during said step (a) accelerates the speed with which said step (a) is conducted.

11. The method of claim 1, wherein said at least one sequential reactor comprises a single reactor, further comprising the step of:
(n) maintaining, during performance of said steps (a) to (d), a reactor pressure between about 1 atm, to about 7 atm.

12. The method of claim 1, wherein, when said step (e) is performed, said step (e) comprises the step of treating said oxidate by an aqueous $NH_3$ solution.

13. The method of claim 12, further comprising the step of:
(o) prior to said step (a), determining at least one of concentration value and quantity of said aqueous $NH_3$ solution used for treating said oxidate, based on at least one of: expected cumene conversion degree, expected temperature in each of said at least one sequential reactor, and whether said at least one sequential reactor comprises a plurality of sequential reactors.

14. The method of claim 12, further comprising the steps of:
(p) monitoring values of at least one of: a quantity of organic acids developing during performance of said step (a), a degree of cumene conversion, and temperature in each of said at least once sequential reactor; and
(q) in response to said at least one value determined at said step (p) and to a quantity of said at least one sequential reactor, prior to said step (c), determining at least one of a quantity and concentration of said aqueous $NH_3$ solution.

15. The method of claim 12 further comprising the step of:
(r) during performance of said step (c), maintaining a pH value of said oxidate within a range of about 5 to about 7.

16. The method of claim 15, wherein said step (r) comprises the steps of:
(s) monitoring said pH value of said oxidate during performance of said step (c); and
(t) when said pH value approaches a value of about 5 or about 7, adjusting at least one of a quantity and concentration of said aqueous $NH_3$ solution.

17. The method of claim 12, wherein said aqueous $NH_3$ solution comprises an $NH_3$ concentration of about 0.1 wt. % to about 20 wt. %.

18. The method of claim 1, wherein said oxidate comprises from about 18 to about 30 wt. % CHP, and at least one additional byproduct, further comprising the step of
(u) after a final performance of said step (b), directing said oxidate to a CHP concentration stage to produce technical CHP having about 60 wt. % to about 95 wt. % of a predetermined target product CHP value, and no more than about 20 ppm of organic acids.

19. The method of claim 1, wherein said at least one reaction inhibitor is at least one of: organic acid, phenol, and a sulfur-containing product.

20. A continuous method for producing cumene hydroperoxide (CHP) through cumene oxidation by air oxygen in at least one sequential reactor, comprising the steps of:
(a) conducting the cumene oxidation reaction in one of said at least one sequential reactor until a predetermined threshold CHP concentration is reached;
(b) discharging an oxidate from said one of said at least one sequential reactor;
(c) selectively causing contact between said oxidate and an aqueous base solution, to remove at least one reaction inhibitor, such that after said contact, said oxidate comprises an aqueous phase and an organic phase, wherein said step (c) is performed at least once while maintaining a pH value of said oxidate within a range of about 5 to about 7"; and
(d) selectively physically separating said aqueous phase from said organic phase, and:
(1) when said at least one sequential reactor comprises a single reactor, recycling said organic phase to said single reactor to perform said steps (a) to (d) until a predetermined required CHP concentration is achieved, and
(2) when said at least one sequential reactor comprises a plurality of sequential reactors passing said organic phase to a next plural sequential reactor to perform said steps (a) to (d) until said predetermined required CHP concentration is achieved, and recycling said organic phase to a first of said plural sequential reactors when said step (a) has been performed in a last plural sequential reactor and said predetermined required CHP concentration has not yet been achieved.

* * * * *